(12) United States Patent
Bhise et al.

(10) Patent No.: US 8,378,129 B2
(45) Date of Patent: Feb. 19, 2013

(54) TWO-STAGE CALCINATION FOR CATALYST PRODUCTION

(75) Inventors: Vijay S. Bhise, North Caldwell, NJ (US); Arie Bortinger, Ridgewood, NJ (US); Stephen R. Allen, Morris Plains, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 0 days.

(21) Appl. No.: 13/280,962

(22) Filed: Oct. 25, 2011

(65) Prior Publication Data

US 2012/0041217 A1 Feb. 16, 2012

Related U.S. Application Data

(62) Division of application No. 11/500,833, filed on Aug. 8, 2006, now Pat. No. 8,097,557.

(51) Int. Cl.
| | |
|---|---|
| C07D 301/03 | (2006.01) |
| C07D 301/10 | (2006.01) |
| B01J 21/00 | (2006.01) |
| B01J 21/04 | (2006.01) |
| B01J 20/00 | (2006.01) |
| B01J 23/00 | (2006.01) |
| B01J 23/02 | (2006.01) |
| B01J 23/48 | (2006.01) |
| B01J 23/50 | (2006.01) |

(52) U.S. Cl. ........ 549/523; 549/534; 549/535; 549/536; 549/537; 502/243; 502/347; 502/348; 502/355; 502/415; 502/439

(58) Field of Classification Search ................... 549/523, 549/534, 535, 536, 537; 502/243, 347, 348, 502/355, 415, 439
See application file for complete search history.

(56) References Cited

U.S. PATENT DOCUMENTS

| | | | |
|---|---|---|---|
| 3,775,346 A | 11/1973 | Calcagno et al. | |
| 3,793,231 A | 2/1974 | Bergmann et al. | |
| 4,774,222 A | 9/1988 | Rashkin | |
| 4,820,675 A | 4/1989 | Lauritzen | |
| 5,364,826 A | 11/1994 | Kemp | |
| 5,418,202 A | 5/1995 | Evans et al. | |
| 5,504,052 A | 4/1996 | Rizkalla et al. | |
| 5,545,603 A | 8/1996 | Kemp | |
| 5,597,773 A | 1/1997 | Evans et al. | |
| 5,646,087 A | 7/1997 | Rizkalla et al. | |
| 5,739,075 A | 4/1998 | Matusz | |
| 5,801,259 A | 9/1998 | Kowaleski | |
| 5,856,534 A * | 1/1999 | Cooker et al. | 549/534 |
| 5,929,259 A | 7/1999 | Lockemeyer | |
| 5,945,551 A * | 8/1999 | Rizkalla et al. | 549/534 |
| 5,958,824 A | 9/1999 | Rizkalla et al. | |
| 6,114,553 A * | 9/2000 | Kiriki et al. | 549/534 |
| 6,143,261 A | 11/2000 | Lissy et al. | |
| 6,281,370 B1 * | 8/2001 | Shima et al. | 549/536 |
| 6,372,925 B1 * | 4/2002 | Evans et al. | 549/536 |
| 6,717,001 B2 * | 4/2004 | Evans et al. | 549/536 |
| 6,762,311 B2 | 7/2004 | Rizkalla et al. | |
| 7,485,597 B2 | 2/2009 | Lockemeyer et al. | |
| 7,504,525 B2 * | 3/2009 | Lockemeyer | 549/534 |
| 7,507,844 B2 * | 3/2009 | Pak | 549/534 |
| 2006/0205963 A1 | 9/2006 | Rubinstein et al. | |
| 2006/0252639 A1 | 11/2006 | Pak et al. | |
| 2008/0306289 A1 | 12/2008 | Matusz et al. | |

OTHER PUBLICATIONS

U.S Final Official Action dated Aug. 17, 2011 related to U.S. Appl. No. 11/500,833.
U.S Official Action dated Feb. 22, 2011 related to U.S. Appl. No. 11/500,833.
U.S Final Official Action dated Aug. 26, 2010 related to U.S. Appl. No. 11/500,833.
U.S Final Official Action dated Dec. 8, 2009 related to U.S. Appl. No. 11/500,833.
U.S Official Action dated May 8, 2009 related to U.S. Appl. No. 11/500,833.

* cited by examiner

*Primary Examiner* — Cam N. Nguyen
(74) *Attorney, Agent, or Firm* — Scully, Scott, Murphy & Presser, P.C.

(57) ABSTRACT

The invention relates to an improved process for producing a catalyst useful for the epoxidation of ethylene to ethylene oxide. In forming the catalyst, a silver-impregnated support is subjected to two calcinations. The support is subjected to a first calcination in a first atmosphere comprising air. Next the support is subjected to a second calcination in a second atmosphere which is substantially entirely comprised of inert gas, and which second atmosphere is substantially absent of hydrogen. This two-stage calcination produces an improved catalyst which contains fewer organics left over under standard conditions of air calcination alone, while costing less than calcination in an inert gas alone.

26 Claims, No Drawings

TWO-STAGE CALCINATION FOR CATALYST PRODUCTION

CROSS REFERENCE TO RELATED APPLICATIONS

The present application is a divisional of copending application Ser. No. 11/500,833 filed on Aug. 8, 2006, the entire contents of which are incorporated by reference herein.

BACKGROUND OF THE INVENTION

1. Field of the Invention

The invention relates to an improved process for producing a catalyst useful for the epoxidation of ethylene to ethylene oxide. It relates to a process wherein a solid support is impregnated with a silver-containing compound and one or more optional promoters, and is calcined to convert the impregnated support into a catalyst. The improvement of this process is that a two-stage calcination is conducted. That is, the impregnated support is subjected to a first calcination in an air atmosphere, and a second calcination in an inert gas atmosphere.

2. Description of the Related Art

In the catalytic epoxidation of ethylene, modern silver-based supported catalysts are highly selective towards ethylene oxide production. Preparation of such catalysts typically involves impregnating a solid support with a silver solution and optional promoters such as transition metals or alkali metals, and thereafter calcining the impregnated support in order to reduce the silver solution to metallic silver, and to separate volatiles from the catalyst. U.S. Pat. No. 4,916,243 shows silver catalysts for ethylene oxidation to ethylene oxide prepared by impregnating an inert support with a silver/amine and silver lactate solutions. The impregnated carriers are than heat treated on steel belt transported through a heating zone for 2.5 minutes, the heating zone being maintained at 500° C. by passing hot air upward through the belt, or at 400° C. for 4 minutes.

It is further known in the art to conduct the calcination/heating of such impregnated supports in a nitrogen atmosphere. For example, U.S. Pat. No. 5,444,034 relates to silver catalyst preparation wherein a support is impregnated with a hydrocarbon solution of a silver salt of an organic acid and activated in stages up to a temperature of 500° C. under an inert gas such as nitrogen.

While several conventional processes conduct their calcinations in inert gas atmospheres such as nitrogen, these inert gas calcinations are expensive. Attempts have thus been made to calcine an impregnated support in an air atmosphere, to reduce costs. However, several disadvantages result from calcination in air alone. First, it has been observed that air calcination of an impregnated support produces a gray-black material that is less uniform in color than a catalyst which is produced by calcination in an inert gas such as nitrogen. Air calcination is typically conducted at lower temperatures to ensure that the catalyst is not damaged in the production process. This lower temperature calcination undesirably leaves greater amounts of residual organic species on the surface of the produced catalyst than during a higher temperature nitrogen calcination. Thus it takes longer to remove the residual organic species resulting from an air calcination process than from a nitrogen calcination during catalyst start up. This represents lost production time as well as reduction in the profitablility of the process.

It has now been unexpectedly found that it is beneficial to conduct two calcinations of an impregnated support. According to this invention, a first calcination is conducted in an air atmosphere, and a second calcination is conducted in an inert gas atmosphere, such as a nitrogen atmosphere. This two-stage calcination produces an improved catalyst which takes less time to manufacture, and contains fewer organics left over under standard conditions of air calcination alone, while costing less than calcination in an inert gas alone.

SUMMARY OF THE INVENTION

The invention provides a process for producing a catalyst useful for the oxidation of ethylene to ethylene oxide which comprises:

(a) providing an impregnated solid support having a surface, which support has been impregnated with a catalytically effective amount of silver or a silver-containing compound on the support, and one or more optional promoters on the support;

(b) subjecting the impregnated solid support to a first calcination in a first atmosphere comprising air; and (c) thereafter subjecting the impregnated solid support to a second calcination in a second atmosphere which is substantially entirely comprised of inert gas, and which second atmosphere is substantially absent of hydrogen.

The invention further provides a process for producing a catalyst useful for the oxidation of ethylene to ethylene oxide which comprises:

(a) providing an impregnated solid support having a surface, which support has been impregnated with a catalytically effective amount of silver or a silver-containing compound on the support, a promoting amount of rhenium or a rhenium-containing compound on the support, and a promoting amount of one or more alkali metals, or one or more alkali-metal-containing compounds on the support;

(b) subjecting the impregnated solid support to a first calcination in a first atmosphere comprising air; and (c) thereafter subjecting the impregnated solid support to a second calcination in a second atmosphere which is substantially entirely nitrogen, and which second atmosphere is substantially absent of hydrogen.

The invention still further provides a catalyst produced by a process comprising:

(a) providing an impregnated solid support having a surface, which support has been impregnated with a catalytically effective amount of silver or a silver-containing compound on the support, and one or more optional promoters on the support;

(b) subjecting the impregnated solid support to a first calcination in a first atmosphere comprising air; and (c) thereafter subjecting the impregnated solid support to a second calcination in a second atmosphere which is substantially entirely comprised of inert gas, and which second atmosphere is substantially absent of hydrogen.

DETAILED DESCRIPTION OF THE INVENTION

This invention relates to an improved process for producing a catalyst which is useful for the oxidation of ethylene to ethylene oxide. This process includes a two-phase calcination wherein an impregnated support is subjected to a first calcination in an air atmosphere, and a second calcination in an inert gas atmosphere, in producing the inventive catalyst.

The inventive process includes first providing an impregnated solid support having a surface, which support has been impregnated with a catalytically effective amount of silver or a silver-containing compound on the support, and one or more optional promoters. In one embodiment, the impregnated support has a surface area of from about 0.2 m²/g to about 2 m²/g.

The support employed in this invention may be selected from a large number of solid, refractory supports that may be porous or non-porous. Alumina is well known to be useful as a catalyst support for the epoxidation of an olefin and is the preferred support. The particular alumina may be porous or non-porous. The alumina support may also contain various impurities and additives which may or may not influence the catalytic epoxidation reaction. Such solid supports may be purchased commercially. In a process for making the preferred alumina support, high-purity aluminum oxide, preferably alpha-alumina, is thoroughly mixed with temporary and permanent binders. The temporary binders, known as burnout materials, are thermally decomposable organic compounds of moderate to high molecular weight which, on decomposition, alter the pore structure of the support. The permanent binders are typically inorganic clay-type materials having fusion temperatures below that of the alumina and impart mechanical strength to the finished support. After thorough dry-mixing, sufficient water or other suitable liquid is added to help form the mass into a paste-like substance. Catalyst support particles are then formed from the paste by conventional means such as extrusion. The particles are then dried and are subsequently calcined at an elevated temperature.

U.S. patents which describe the production of alumina supports include U.S. Pat. Nos. 2,499,675, 2,950,169 and 3,172,866. Other patents such as U.S. Pat. Nos. 3,222,129, 3,223,483 and 3,226,191 show the preparation of active aluminas. Methods of making highly porous aluminas are disclosed in U.S. Pat. Nos. 3,804,781, 3,856,708, 3,907,512 and 3,907,982. Alumina carriers having high thermal stability are disclosed in U.S. Pat. No. 3,928,236. Other improvements in making catalyst carriers are discussed in U.S. Pat. Nos. 3,987,155, 3,997,476, 4,001,144, 4,022,715; 4,039,481, 4,098,874 and 4,242,233. Other processes for making supports are described, for instance in U.S. Pat. Nos. 4,575,494, 3,172,866, 4,356,113, 4,082,697, 4,001,144, 3,856,708, 3,850,849 and 3,526,602.

The support may comprise materials such as alpha-alumina, charcoal, pumice, magnesia, zirconia, titania, kieselguhr, Fuller's earth, silicon carbide, silica, silicon carbide, magnesia, clays, artificial zeolites, natural zeolites, ceramics, or combinations thereof. The preferred support is comprised of alpha-alumina having a very high purity; i.e., at least 95 wt. % pure, or more preferably, at least 98 wt. % alpha-alumina. The remaining components may include aluminas other than alpha-alumina, such as silica, alkali metal oxides (e.g., sodium oxide) and trace amounts of other metal-containing or non-metal-containing additives or impurities. A wide variety of such supports are commercially available. Suitable alumina carriers are manufactured and generally commercially available from Süd-Chemie Inc., of Louisville, Ky., and Saint-Gobain Norpro, of Stow, Ohio.

Certain types of alpha alumina-containing supports are particularly preferred. These alpha alumina supports have relatively uniform pore diameters and are more fully characterized by having a B.E.T. surface area of from about 0.03 m²/g to about 10 m²/g, preferably from about 0.05 m²/g to about 5 m²/g, more preferably from about 0.1 m²/g to about 3 m²/g; and pore volumes of from about 0.10 cc/g to about 0.85 cc/g, preferably from about 0.25 cc/g to about 0.75 cc/g. Median pore diameters for these supports range from about 0.5 micrometers to about 50 micrometers. The supports may have mono-modal, bimodal or multimodal pore distributions. The surface acidity of the support, as determined by irreversible ammonia sorption at 100° C., is often less than about 2 micromoles per gram of support, preferably less than about 1.5 micromoles per gram of support, and often from about 0.05 to 1.0 about micromoles per gram of support.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range of from about 3 mm to about 10 mm and preferably in the range of from about 4 mm to about 8 mm, which are usually compatible with the internal diameter of the tubular reactors in which the catalyst is placed. Equivalent diameter is the diameter of a sphere having the same external surface (i.e. neglecting surface within the pores of the particle) to volume ratio as the support particles being employed.

A suitable support of the present invention can be purchased commercially, or prepared by a variety of methods, for example, by mixing the refractory material, such as alumina, water or other suitable liquid, a burnout material or suitable porosity-controlling agent, and a binder. Burnout materials include cellulose, substituted celluloses, e.g. methylcellulose, ethylcellulose, and carboxyethylcellulose, stearates, such as organic stearate esters, e.g. methyl or ethyl stearate, waxes, granulated polyolefins, particularly polyethylene and polypropylene, walnut shell flour, and the like which are decomposable at the firing temperatures used in preparation of the support. The burnout is used to modify the porosity of the support. It is essentially totally removed during the firing to produce the finished support. Supports of the present invention are preferably made with the inclusion of a bonding material such as silica with an alkali metal compound in sufficient amount to substantially prevent the formation of crystalline silica compounds. Appropriate binders include inorganic clay-type materials. A particularly convenient binder material is a mixture of boehmite, an ammonia stabilized silica sol, and a soluble sodium salt. A paste is formed by mixing the dry ingredients of the support with water or other suitable liquid, and the paste is usually extruded or molded into the desired shape, and then fired or calcined at a temperature of from about 1200° C. to about 1600° C. to form the support. When the particles are formed by extrusion, it may be desirable to also include extrusion aids. The amounts of extrusion aids required will depend on a number of factors that relate to the equipment used. However these matters are well within the general knowledge of a person skilled in the art of extruding ceramic materials. After firing, the support is preferably washed to remove soluble residues. Washing is most commonly done with water but washing with other solvents or aqueous/non-aqueous solutions can also be beneficial.

In order to produce a catalyst for the oxidation of ethylene to ethylene oxide, a support having the above characteristics is provided with a catalytically effective amount of silver on its surface. That is, the catalyst is prepared by impregnating a washed or unwashed support with silver or a silver-containing compound, which may include a silver complex or salt, preferably dissolved in a suitable solvent sufficient to form a solution, and to cause deposition of metallic silver onto the support. The silver-containing compound preferably comprises an aqueous silver solution. After impregnation, excess solution is removed from the impregnated support, and the impregnated support is heated, or calcined, to evaporate the solvent and to deposit the silver or silver compound on the support, as is known in the art.

The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Suitable silver-containing compounds useful as silver precursors non-exclusively include silver oxalate, silver nitrate, silver oxide, silver carbonate, a silver carboxylate, silver citrate, silver phthalate, silver lactate, silver propionate, silver butyrate and higher fatty acid salts or combinations thereof.

The silver containing compound may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the silver containing compound comprises an aqueous solution of silver oxalate and ethylene diamine. In another preferred embodiment, the silver containing compound comprises an aqueous solution of silver oxalate and ethanol amine. The complexing/solubilizing agent may be present in the impregnating solution in an amount of from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Examples of organic solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of several organic solvents or mixtures of organic solvent(s) with water may be used, provided that such mixed solvents function as desired herein.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution Impregnation procedures are described in U.S. Pat. Nos. 4,761,394, 4,766,105, 4,908,343, 5,057,481, 5,187,140, 5,102,848, 5,011,807, 5,099,041 and 5,407,888. Known procedures of pre-deposition, co-deposition and post-deposition of various promoters can be employed.

The concentration of silver in the impregnating solution is typically in the range of from about 0.1% by weight up to the maximum solubility afforded by the particular solvent/solubilizing agent combination employed. It is generally very suitable to employ solutions containing from 0.5% to about 45% by weight of silver, with concentrations of from 5 to 30% by weight of silver being preferred.

Preferred catalysts prepared in accordance with this invention contain up to about 45% by weight of silver, expressed as metal, deposited upon the surface of the support. Should the support be porous, the silver may be deposited upon the porous surface and throughout the pores of a porous refractory support. Silver contents, expressed as metal, of from about 1% to about 40% based on the total weight of the catalyst are preferred, while silver contents of from about 8% to about 35% are more preferred.

Optionally but preferably, the solid support may further be impregnated with one or more promoters on the support. Such may be done either prior to, coincidentally with, or subsequent to the deposition of the silver. When present, the promoter is preferably in the form of a promoting amount of one or more transition metals, one or more transition metal-containing compounds, one or more alkali metals, one or more alkali-metal-containing compounds, or combinations thereof, on the surface of the support. Should the support be porous, the promoter may be deposited upon the porous surface and throughout the pores of a porous refractory support.

In one preferred embodiment, the promoter comprises a promoting amount of a rhenium component on the support. This may be in the form of rhenium, a rhenium-containing compound or a rhenium-containing complex. The rhenium promoter may be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the rhenium metal.

In another embodiment, the solid support may be impregnated with additional optional promoters, such as those including promoting amounts of one or more alkali metals, one or more Group IIA alkaline earth metal-containing components, or one or more transition metal-components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably the amount will range from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metal-containing compounds comprise molybdenum, tungsten, chromium, titanium, hafnium, zirconium, vanadium, thorium, tantalum, niobium, or combinations thereof. In one preferred embodiment, the transition metal-containing compound comprises molybdenum or tungsten, or combinations thereof.

The amount of alkaline earth metal promoter(s) and/or transition metal promoter(s) deposited on the support is a promoting amount. The transition metal promoter may typically be present in an amount of from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal.

The support may further comprise a promoting amount of one or more sulfur or sulfur-containing compounds, one or more phosphorus or phosphorus-containing compounds, one or more boron or boron-containing compounds, one or more halogen or halogen-containing compounds, one or more gallium or gallium-containing compounds, one or more germanium or germanium containing compounds, or combinations thereof, on the support. Suitable solid supports are well known in the art, and may be purchased commercially.

After impregnation of the support with the silver-containing compound and one or more optional promoters, the impregnated support is calcined for a time sufficient to convert the silver containing compound to an active silver species, and to remove any organics and/or volatile components from the impregnated support, resulting in the formation of a catalyst.

A key feature of the inventive process is a two-stage calcination of the impregnated support. That is, two calcinations are conducted. A first calcination is done in a first atmosphere comprising air. A subsequent second calcination is done in a second atmosphere, which second atmosphere is substantially entirely comprised of inert gas, and which second atmosphere is substantially absent of hydrogen. The first and second calcination steps may be done continuously or discontinuously with each other, and may be conducted in a single apparatus or separate apparatuses.

For purposes of this invention, inert gases are defined as those which do not substantially react with the catalyst, or catalyst-producing components under the catalyst preparation conditions chosen. Suitable inert gases include nitrogen, helium, argon, carbon dioxide and neon and combinations thereof, with the preferred inert gas being nitrogen. For purposes of this invention, carbon dioxide is considered an inert gas. In a preferred embodiment, the second atmosphere is substantially entirely nitrogen. In a most preferred embodiment, the second atmosphere is entirely nitrogen. As stated above, the second atmosphere is preferably substantially absent of hydrogen. In a preferred embodiment the second atmosphere is absent of hydrogen.

The calcinations are conducted by heating the impregnated support, preferably at a gradual rate. The first calcination, which is conducted in an air atmosphere, is preferably conducted at a temperature of up to about 270° C., preferably from about 100° C. to about 270° C., more preferably from about 100° C. to about 250° C., and most preferably from about 130° C. to about 240° C. In one preferred embodiment, the temperature of the first calcination is maintained within a range of up to about 250° C., followed by periodic temperature spikes up to 270° C., and subsequently followed by a decrease of the temperature back within the range of about 250° C. or less.

The second calcination, which is conducted in an inert gas atmosphere, is preferably conducted at a temperature which is higher than that of the first calcination. The second calcination step is preferably conducted at a temperature of about 200° C. or higher. In a preferred embodiment, the second calcination step is conducted at a temperature of from about 200° C. to about 600° C., more preferably from about 250° C. to about 500° C., and most preferably from about 350° C. to about 400° C. In another preferred embodiment, the second calcination is conducted at a temperature which is from about 235° C. to about 450° C. Higher or lower temperatures are possible. In further embodiments of this invention, additional calcinations in additional atmospheres may be conducted.

It is important that the heating time be correlated with the temperature such that substantially all of the contained silver is converted to the active silver species. Continuous or stepwise heating may be used for this purpose. In one preferred embodiment, the first calcination and/or second calcination is conducted for about 1 minute to about 2 hours. In another embodiment, the first calcination and/or second calcination is conducted for about 5 minutes to about 1 hour. In still another embodiment, the first calcination and/or second calcination is conducted for about 10 minutes to about 30 minutes.

Ethylene Oxide Production

The epoxidation process may be carried out by continuously contacting an oxygen-containing gas with an olefin, which is preferably ethylene, in the presence of the catalyst produced by the invention. Oxygen may be supplied to the reaction in substantially pure molecular form or in a mixture such as air. Molecular oxygen employed as a reactant may be obtained from conventional sources. Reactant feed mixtures may contain from about 0.5% to about 45% ethylene and from about 3% to about 15% oxygen, with the balance comprising comparatively inert materials including such substances as carbon dioxide, water, inert gases, other hydrocarbons, and one or more reaction modifiers such as organic halides. Non-limiting examples of inert gases include nitrogen, helium, argon, neon, and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride or mixtures thereof. Most preferred reaction moderators are ethyl chloride and ethylene dichloride. Usually such reaction moderators are employed in an amount of from about 0.5 to 10 ppmv, preferably from 2 to 8 ppmv of the total volume of the feed gas.

A usual method for the ethylene epoxidation process comprises the vapor-phase oxidation of ethylene with molecular oxygen, in the presence of the inventive catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst. Typical operating conditions for the ethylene epoxidation process involve temperatures in the range of from about 180° C. to about 330° C., and preferably, about 200° C. to about 325° C., and more preferably from about 225° C. to about 270° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1-5 seconds. The present catalysts are effective for this process when operated within these ranges of conditions.

The resulting ethylene oxide is separated and recovered from the reaction products using conventional methods. For this invention, the ethylene epoxidation process may include a gas recycle wherein substantially all of the reactor effluent is readmitted to the reactor inlet after substantially or partially removing the ethylene oxide product and the byproducts. In the recycle mode, carbon dioxide concentrations in the gas inlet to the reactor may be, for example, from about 0.5 to 6 volume percent.

The inventive catalysts have been shown to be particularly selective for oxidation of ethylene with molecular oxygen to ethylene oxide. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity of 1500-10,000 $h^{-1}$, a reactor inlet pressure of 150-400 psig, a coolant temperature of 180-315° C., an oxygen conversion level of 10-60%, and an EO production rate (work rate) of 2-16 lbs. EO/cu.ft. catalyst/hr. The feed composition at the reactor inlet may typically comprises 1-40% ethylene, 3-12% $O_2$, 2-40% $CO_2$, 0-3% ethane, 0.3-20 ppmv total concentration of organic chloride moderator(s), and the balance of the feed being comprised of argon, methane, nitrogen or mixtures thereof.

The following non-limiting examples serve to illustrate the invention.

Example 1

A catalyst was prepared according to the procedures described in Example 1 of U.S. Pat. No. 6,858,560 except the catalyst here was prepared to contain about 11.5% silver and 475 ppm Cs. The calcination step was carried out in air, with the temperature being controlled to remain below 300° C. The carbon and nitrogen analysis results for this material after air calcination are shown in Table 1. The catalyst was then subjected to a second calcination step, under nitrogen, to allow the temperature to reach up to 400° C. The carbon and nitrogen analysis results for this material after nitrogen calcination are shown in Table 1. The nitrogen analyses were determined using the Kejeldahl analytical method.

TABLE 1

| Example # 1 | % Carbon | % Nitrogen |
|---|---|---|
| Air Calcination | 0.256 | 0.130 |
| Second Calcination in Nitrogen | 0.094 | 0.061 |

The results show that the second calcination significantly reduces the volatiles on the catalyst.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the oxidation of ethylene to ethylene oxide, the process comprising:
   providing an impregnated solid support having a surface, which support has been impregnated with at least a catalytically effective amount of silver metal or a silver-containing compound;
   subjecting the impregnated solid support to a first calcination in a first atmosphere comprising air, wherein said first calcination is maintained at a temperature of about 250° C. with periodic temperature spikes up to 270° C.;
   thereafter subjecting the impregnated solid support to a second calcination in a second atmosphere, which is substantially entirely comprised of an inert gas and substantially absent of hydrogen to produce a catalyst containing active silver species;
   placing said catalyst in a fix-bed, tubular reactor; and
   oxidizing ethylene in the presence of oxygen and said catalyst, wherein said oxidizing is performed in a vapor phase.

2. The process of claim 1, further comprising at least one promoter, wherein said at least one promoter is comprised of an alkali metal promoter included in an amount which promotes activity and/or selectivity of the catalyst.

3. The process of claim 2, wherein said amount of said alkali metal promoter is up to 3,000 ppm.

4. The process of claim 2, further comprising at least one other promoter selected from the group consisting a transition metal and a transition metal-containing compound.

5. The process of claim 4 wherein the transition metal comprises an element selected from the group consisting of Groups IVA, VA, VIA, VIIA and VIIIA of the Periodic Table of the Elements, and combinations thereof.

6. The process of claim 5 wherein the transition metal comprises molybdenum, tungsten, chromium, titanium, hafnium, zirconium, vanadium, thallium, thorium, tantalum, niobium, or a combination thereof.

7. The process of claim 5 wherein the transition metal comprises molybdenum, tungsten, or a combination thereof.

8. The process of claim 2, further comprising at least one other promoter, wherein said at least one other promoter is a Group IIA metal-containing compound.

9. The process of claim 8 wherein the Group IIA metal-containing compound comprises beryllium, magnesium, calcium, strontium, barium, or a combination thereof.

10. The process of claim 2 wherein said alkali metal promoter is selected from the group consisting of lithium, sodium, potassium, rubidium, cesium and a combination thereof.

11. The process of claim 10 wherein said alkali metal promoter comprises cesium.

12. The process of claim 1 wherein the inert gas comprises nitrogen, helium, argon, neon, carbon dioxide, or combinations thereof.

13. The process of claim 1 wherein the second atmosphere is substantially entirely nitrogen.

14. The process of claim 1 wherein the second atmosphere is entirely nitrogen.

15. The process of claim 1 wherein the second atmosphere is absent of hydrogen.

16. The process of claim 1 wherein the first calcination and/or second calcination is conducted for about 1 minute to about 2 hours.

17. The process of claim 1 wherein the support is alumina, charcoal, pumice, magnesia, zirconia, titania, kieselguhr, fuller's earth, silicon carbide, silica, clays, artificial zeolites, natural zeolites, ceramics or a combination thereof.

18. The process of claim 1 wherein the support comprises alumina and the support surface is porous.

19. The process of claim 1 wherein the impregnated solid support has a surface area of from about 0.2 $m^2/g$ to about 2 $m^2/g$.

20. The process of claim 1 wherein the silver-containing compound is silver oxalate, silver nitrate, silver oxide, silver carbonate, a silver carboxylate, silver citrate, silver phthalate, silver lactate, silver propionate, silver butyrate, silver fatty acid salts or a combination thereof.

21. The process of claim 1 further comprising at least one promoter selected from consisting of a rhenium compound and a rhenium-containing compound.

22. A catalyst produced by a process comprising:
(a) providing an impregnated solid support having a surface, which support has been impregnated with at least a catalytically effective amount of silver metal or a silver-containing compound;
(b) subjecting the impregnated solid support to a first calcination in a first atmosphere comprising air, wherein said first calcination is maintained at a temperature of about 250° C. with periodic temperature spikes up to 270° C.; and
(c) thereafter subjecting the impregnated solid support to a second calcination in a second atmosphere, which is substantially entirely comprised of an inert gas and substantially absent of hydrogen, wherein said catalyst has a reduced amount of organic and/or volatile components as compared to a catalyst produced by air calcination alone.

23. The catalyst of claim 22, further comprising at least one promoter, wherein said at least one promoter is comprised of an alkali metal promoter included in an amount which promotes activity and/or selectivity of the catalyst.

24. The catalyst of claim 23, wherein said amount of said alkali metal promoter is up to 3,000 ppm.

25. The catalyst of claim 23, further comprising at least one other promoter selected from the group consisting of a transition metal and a transition metal-containing compound.

26. The catalyst of claim 23, further comprising at least one other promoter, wherein said at least one other promoter is a Group IIA metal-containing compound.

* * * * *